(12) United States Patent  
Harding et al.

(10) Patent No.: US 9,188,551 B2  
(45) Date of Patent: Nov. 17, 2015

(54) ANGLE-DEPENDENT X-RAY DIFFRACTION IMAGING SYSTEM AND METHOD OF OPERATING THE SAME

(71) Applicant: MORPHO DETECTION, INC., Newark, CA (US)

(72) Inventors: Geoffrey Harding, Hamburg (DE); Helmut Rudolf Otto Strecker, Hamburg (DE)

(73) Assignee: MORPHO DETCTION, LLC, Newark, CA (US)

( * ) Notice: Subject to any disclaimer, the term of this patent is extended or adjusted under 35 U.S.C. 154(b) by 55 days.

(21) Appl. No.: 14/033,025

(22) Filed: Sep. 20, 2013

(65) Prior Publication Data

US 2015/0085983 A1    Mar. 26, 2015

(51) Int. Cl.
*G01N 23/201* (2006.01)
*G01N 23/20* (2006.01)
*G01V 5/00* (2006.01)

(52) U.S. Cl.
CPC .............. *G01N 23/201* (2013.01); *G01N 23/20* (2013.01); *G01V 5/0025* (2013.01); *G01N 2223/3307* (2013.01); *G01N 2223/643* (2013.01)

(58) Field of Classification Search
CPC ... G01V 5/0016; G01V 5/0025; G01N 23/04; G01N 23/203; G01N 23/201; A61B 6/483
USPC .............................................. 378/70, 71, 87
See application file for complete search history.

(56) References Cited

U.S. PATENT DOCUMENTS

| | | |
|---|---|---|
| 7,756,249 B1 | 7/2010 | Harding |
| 7,835,495 B2 | 11/2010 | Harding |
| 8,139,717 B2 | 3/2012 | Harding et al. |
| 2006/0093090 A1 | 5/2006 | He |
| 2010/0329424 A1 | 12/2010 | Harding et al. |
| 2011/0188632 A1 | 8/2011 | Harding et al. |
| 2012/0263275 A1 | 10/2012 | Harding et al. |

OTHER PUBLICATIONS

Harding et al., "X-ray diffraction imaging with the muliple Inverse Fan Beam topology: Principles, performance and potential for security screening" 2012, Applied Radiation and Isotopes, vol. 70, p. 1228-1237.*

(Continued)

*Primary Examiner* — Glen Kao  
*Assistant Examiner* — Chih-Cheng Kao  
(74) *Attorney, Agent, or Firm* — Armstrong Teasdale LLP (57) ABSTRACT

An x-ray diffraction imaging (XDI) system having a system axis includes at least one x-ray source configured to generate x-rays directed toward an object that includes at least one substance. The at least one x-ray source is further configured to irradiate at least one voxel defined within the object with x-rays arriving from a plurality of directions, each direction defined by an angle of incidence with respect to the system axis. The system also includes at least one detector configured to detect scattered x-rays after the x-rays have passed through the object. The system further includes at least one processor coupled to the at least one detector. The processor is programmed to generate a plurality of XDI profiles of the object voxel. Each XDI profile is a function of an associated angle of incidence.

20 Claims, 4 Drawing Sheets

(56) References Cited

OTHER PUBLICATIONS

Takagi et al., "Single-Crystal X-ray study of Ba2Cu2Te4O11Br2 and its Incommensurately Modulated Superstructure companion" 2008, Chemistry European Journal, vol. 14, p. 3434-3441.*

An International Search Report and Written Opinion, dated Dec. 22, 2014, for co-pending International application No. PCT/US2014/055410 (13 pgs.).

* cited by examiner

ANGLE-DEPENDENT X-RAY DIFFRACTION IMAGING SYSTEM AND METHOD OF OPERATING THE SAME

BACKGROUND OF THE INVENTION

The embodiments described herein relate generally to an x-ray diffraction imaging (XDI) system and, more particularly, to an angle-dependent XDI system.

Known security detection systems are used at travel checkpoints to inspect carry-on and/or checked bags for concealed weapons, narcotics, and/or explosives. At least some known security detection systems include x-ray imaging systems. In an x-ray imaging system, an x-ray source transmits x-rays through an object or a container, such as a suitcase, towards a detector, and the detector output is processed to identify one or more objects and/or one or more materials in the container.

At least some known security detection systems include an XDI system, e.g., a multi-detector inverse fan beam (MIFB) XDI system that uses an inverse fan-beam geometry (a large source and a small detector) and a multi-focus x-ray source (MFXS). At least some known XDI systems provide an improved discrimination of materials, as compared to that provided by other known x-ray imaging systems, by measuring d-spacings between lattice planes of micro-crystals in materials. Further, x-ray diffraction may yield data from a molecular interference function that may be used to identify other materials, such as liquids, in a container.

Known MIFB XDI systems feature an x-ray multisource emitting a multiplicity of x-ray beams, such that each object voxel is irradiated from several different directions, and such that these systems measure spatially-resolved x-ray diffraction profiles of the constituent voxels of inhomogeneous, extended objects. However, currently, all photons belonging to the same object voxel are merely summed to yield an average XDI profile. This average XDI profile has a fourfold dimensionality, i.e., three spatial dimensions defining the voxel location, and one momentum dimension. As such, no provisions are currently made for separately storing angle dimensional information about the measured photons. Such angle dimensional information relates to the direction at which a primary beam irradiates a certain object voxel relative to a system axis. Therefore, since the angle is assumed to be isotropic, no use is currently made in the threat/no threat classification procedure of possible differences in the form of XDI profiles acquired from different irradiation directions for the same voxel.

For liquid, amorphous and micro-crystalline powder samples there is no preferred orientation direction and the XDI profile is independent of irradiation angle. Voxels however containing an appreciable amount of single-crystal material have a statistically-varying preferred orientation direction, and the XDI profile changes according to the relative angles of the primary x-ray beam to this orientation direction and according to the number of crystallites included in a voxel signal. One example of substances whose XDI profiles vary with angle is the class of anisotropic substances, including coarse-grain powders. Since such anisotropic substances have a relatively high degree of single crystal material compared to isotropic substances such as fine powders. Not leveraging use of this anisotropic nature may lead to less than optimum detection performance.

BRIEF DESCRIPTION OF THE INVENTION

In one aspect, an x-ray diffraction imaging (XDI) system is provided. The system has an axis and includes at least one x-ray source configured to generate x-rays directed toward an object that includes at least one substance. The at least one x-ray source is further configured to irradiate at least one voxel defined within the object with x-rays arriving from a plurality of directions, each direction defined by an angle of incidence with respect to the system axis. The system also includes at least one detector configured to detect scattered x-rays after the x-rays have passed through the object. The system further includes at least one processor coupled to the at least one detector. The processor is programmed to generate a plurality of XDI profiles of the object voxel. Each XDI profile is a function of an associated angle of incidence.

In another aspect, one or more non-transitory computer-readable storage media having computer-executable instructions embodied thereon is provided. When executed by at least one processor, the computer-executable instructions cause the processor to generate a plurality of XDI profiles of an object voxel. The object voxel is irradiated with x-rays directed toward an object that includes at least one substance. The x-rays have a plurality of angles of incidence such that each XDI profile is a function of an associated angle of incidence and each angle of incidence is defined with respect to a system axis. Also, when executed by at least one processor, the computer-executable instructions cause the processor to compare the plurality of XDI profiles and discriminate the irradiated object as one of a potential threat and a potential non-threat as a function of comparison of the plurality of XDI profiles.

In a further aspect, a method of performing a security screen of an object that includes at least one substance is provided. The method includes generating a plurality of XDI profiles of an object voxel. The object voxel is irradiated with x-rays directed toward the object. The x-rays have a plurality of angles of incidence such that each XDI profile is a function of an associated angle of incidence and each angle of incidence is defined with respect to a system axis. The method also includes comparing the plurality of XDI profiles and discriminating the irradiated object as one of a potential threat and a potential non-threat as a function of comparison of the plurality of XDI profiles.

BRIEF DESCRIPTION OF THE DRAWINGS

FIGS. 1-4 show exemplary embodiments of the systems and methods described herein.

DETAILED DESCRIPTION OF THE INVENTION

The angle dependent multi-detector inverse fan beam (MIFB) x-ray diffraction imaging (XDI) system described herein facilitates cost-effective enhanced integration of angle data, thus enhancing overall performance of a security scanning system. Specifically, in contrast to many known security scanning systems, the MIFB XDI security screening system as described herein facilitates exploiting angle-dependent XDI data acquired over a range of angles between the primary beam and the system axis, rather than merely using a single angle. More specifically, the MIFB XDI security screening system as described herein using angle-dependent XDI screening enhances detection performance of materials for which the XRD profiles measured from different irradiation directions vary. As such, the MIFB XDI security screening system as described herein facilitates classification into threat/no threat substances explicitly taking into account the angular dependence of XDI data in the form of XDI profiles acquired from different irradiation directions for the same voxel. Therefore, detection of substances, such as the class of anisotropic substances including coarse-grain powders that have XDI profiles that vary with angle because they have a relatively high degree of single crystal material as compared to isotropic substances, such as fine powders.

Figure 1:
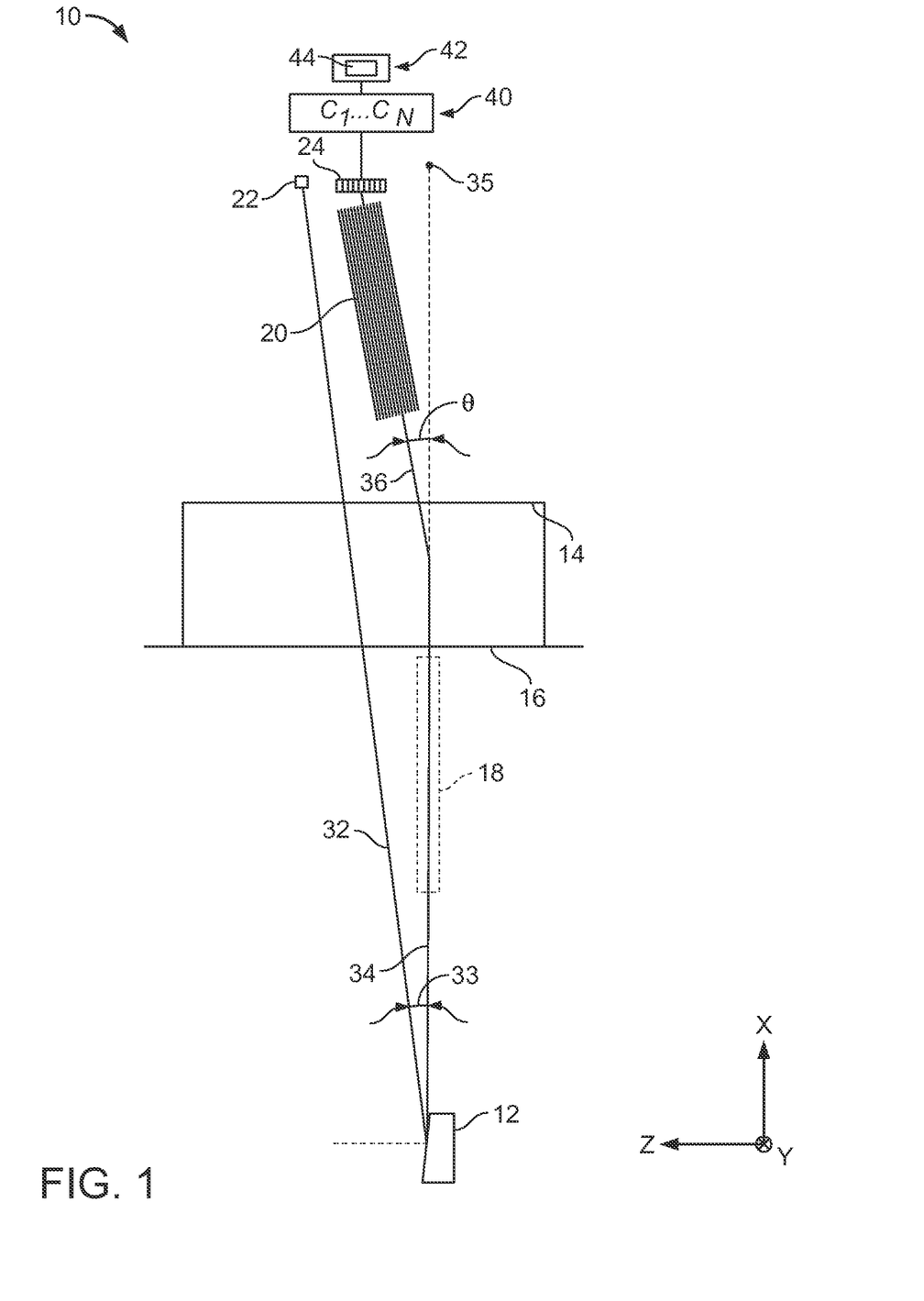
FIG. 1 is a schematic view, in an X-Z plane, of an exemplary security detection system.
Figure 2:
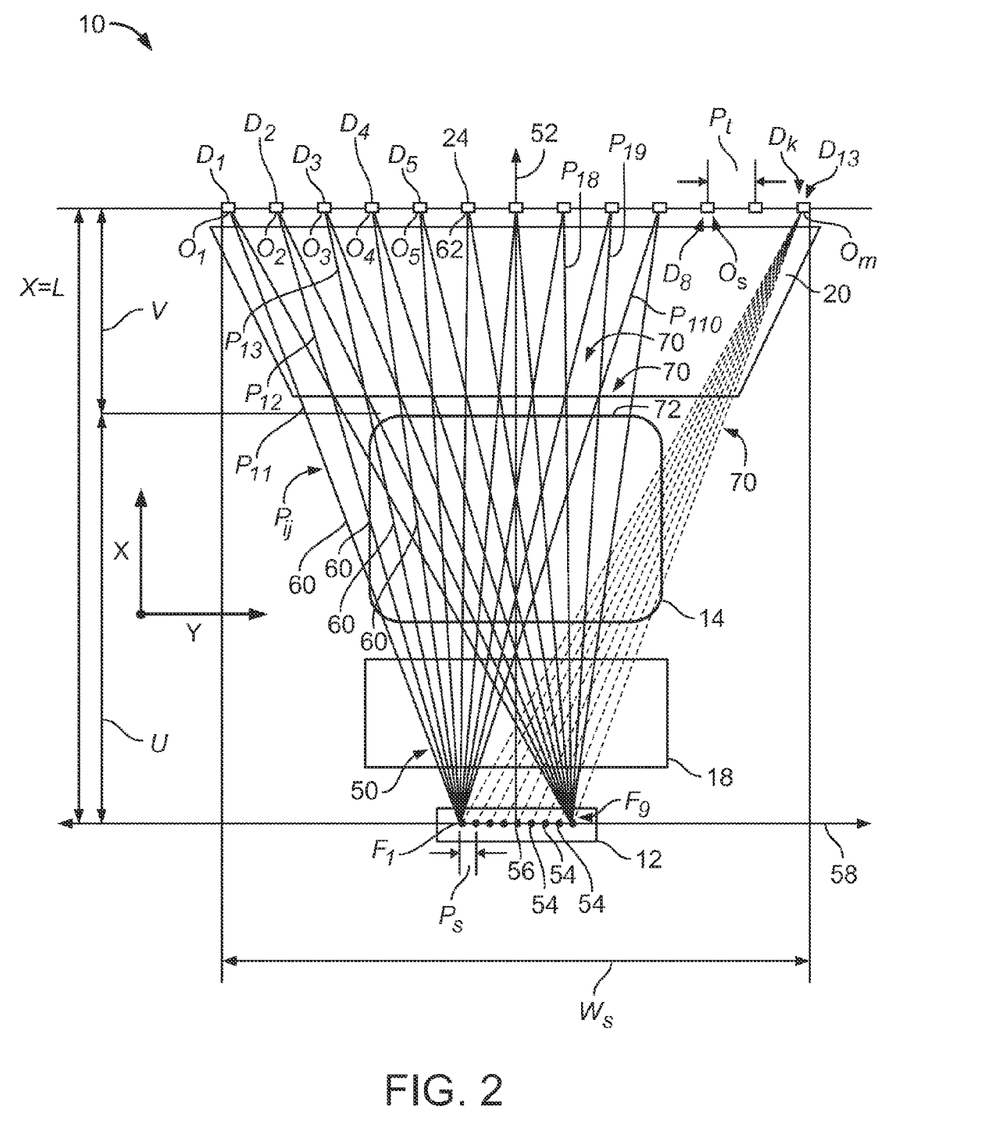
FIG. 2 is a schematic view, in an X-Y plane, of the security detection system shown in FIG. 1.

FIG. 1 is a schematic view, in an X-Z plane, of an exemplary security detection system 10. FIG. 2 is a schematic view, in an X-Y plane, of security detection system 10. In the exemplary embodiment, security detection system 10 is a multi-detector inverse fan beam x-ray diffraction imaging (MIFB XDI) system. Alternatively, security detection system 10 is any XDI system that enables operation of system 10 as described herein. Security detection system 10 includes a multi-focus x-ray source (MFXS) 12, an examination area 14, a support 16 configured to support an object, a primary collimator 18, and a secondary collimator 20. Security detection system 10 also includes two types of detectors, an array of transmission detectors 22 and a plurality of discrete coherent x-ray scatter detectors 24. Transmission detectors 22 are offset in a z-axis direction from coherent x-ray scatter detectors 24.

In the exemplary embodiment, MFXS 12 is capable of emitting x-ray radiation sequentially from a plurality of focus points, as described below, distributed along MFXS 12 in a direction substantially parallel to a y-axis perpendicular to the z-axis. In the exemplary embodiment, MFXS 12 has nine (9) focus points, as shown in FIG. 2. In an alternative embodiment, MFXS 12 has approximately 40 to 100 focus points. Also alternatively, MFXS 12 may include any suitable number of focus points that enables operation of security detection system 10 as described herein.

Further, in the exemplary embodiment, MFXS 12 is located on or coupled to a lower support surface, such as at or near a floor, while transmission detectors 22 and coherent x-ray scatter detectors 24 are located on, or coupled to, an upper support structure, such as at or near a ceiling. In an alternative embodiment, MFXS 12 is located on or coupled to an upper support structure, such as at or near a ceiling, while transmission detectors 22 and coherent x-ray scatter detectors 24 are located on or coupled to a lower support surface, such as at or near a floor. Further, in the exemplary embodiment, MFXS 12, transmission detectors 22 and coherent x-ray scatter detectors 24 are stationary, support 16 is a conveyor belt capable of movement backward and forward in a direction substantially parallel to the z-axis, and examination area 14 is a baggage tunnel through which the conveyor belt moves. In an alternative embodiment, MFXS 12, transmission detectors 22 and coherent x-ray scatter detectors 24 are capable of coordinated movement at least in a direction substantially parallel to the z-axis, and support 16 is stationary. In certain alternative embodiments, MFXS 12, transmission detectors 22, coherent x-ray scatter detectors 24 and support 16 are all capable of movement.

In the exemplary embodiment, MFXS 12 is configured to emit an x-ray fan beam 32 from each focus point of MFXS 12. Each fan beam 32 lies substantially in a plane at an angle 33 relative to a vertical x-axis perpendicular to the z-axis and the y-axis. Each fan beam 32 is directed at transmission detectors 22. In the exemplary embodiment, angle 33 is approximately ten degrees. In an alternative embodiment, angle 33 is approximately fifteen degrees. In further alternative embodiments, angle 33 is any suitable angle that enables security detection system 10 to function as described herein.

In addition, MFXS 12 is configured to emit, through primary collimator 18, a set of x-ray pencil beams 34, from each focus point of MFXS 12. Each pencil beam 34 is directed at a corresponding convergence point 35 which lies in the same X-Y plane as MFXS 12. Further, each convergence point 35 is positioned at the same X-coordinate value, but at different Y-coordinate values. Because each pencil beam 34 is emitted in the same X-Y plane, only one pencil beam 34 (and only one convergence point 35) is visible in the X-Z cross-section view of FIG. 1.

A portion of the x-ray radiation from each pencil beam 34 typically is scattered in various directions upon contact with a container (not shown) in examination area 14. Secondary collimator 20 is configured to facilitate ensuring that a portion of scattered radiation 36 arriving at each coherent x-ray scatter detector 24 has a constant scatter angle $\theta$ with respect to the corresponding pencil beam 34 from which scattered radiation 36 originated. In certain embodiments, scatter angle $\theta$ is approximately 0.04 radians. Coherent x-ray scatter detectors 24 may be positioned between pencil beams 34 and fan beam 32 to ensure that only scattered radiation from the former and not the latter is detected. For example, secondary collimator 20 is configured to absorb scattered radiation (not shown) that is not parallel to the direction of scattered radiation 36. Further, although, in the exemplary embodiment, secondary collimator 20 and coherent x-ray scatter detectors 24 are positioned on one side of pencil beams 34 with respect to the z-axis, in alternative embodiments secondary collimator 20 and coherent x-ray scatter detectors 24 may be positioned on the other side, or on both sides, of pencil beams 34 with respect to the z-axis.

In the exemplary embodiment, transmission detectors 22 are charge integration detectors, while coherent x-ray scatter detectors 24 are pulse-counting energy-resolving detectors. Transmission detectors 22 and each coherent x-ray scatter detector 24 are in electronic communication with a number of channels 40, for example, N number of channels $C_1, \ldots C_N$, wherein N is selected based on the configuration of security detection system 10. Channels 40 electronically communicate data collected by transmission detectors 22 and each coherent x-ray scatter detector 24 to a data processing system 42. In the exemplary embodiment, data processing system 42 combines an output from transmission detectors 22 and an output from coherent x-ray scatter detectors 24 to generate information about the contents of an object positioned within examination area 14. For example, but not by way of limitation, data processing system 42 may generate multiview projections and/or section images of a container (not shown) in examination area 14 that identify a location in the container of specific materials detected by XDI analysis.

In the exemplary embodiment, data processing system 42 includes a processor 44 in electrical communication with transmission detectors 22 and coherent x-ray scatter detectors 24. Processor 44 is configured to receive from coherent x-ray scatter detectors 24 output signals representative of the detected x-ray quanta and generate a distribution of momentum transfer values, x, from a spectrum of energy, E, of x-ray quanta within scattered radiation detected by coherent x-ray scatter detectors 24.

As used herein, the terms "processor" and "processing device" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, e.g., firmware, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Processor 44 and other processors (not shown) as described herein process information transmitted from a plurality of electrical and electronic devices that include, without limitation, transmission detectors 22. Memory devices (not shown) and storage devices (not shown) store and transfer information and instructions to be executed by processor 44. Such memory devices and storage devices can also be used to store and provide temporary variables, static (i.e., non-volatile and non-changing) information and instructions, or other intermediate information to processor 44 during execution of instructions by processor 44. Instructions that are executed include, but are not limited to, analysis of signals transmitted from transmission detectors 22. The execution of sequences of instructions is not limited to any specific combination of hardware circuitry and software instructions.

Referring further to FIG. 2, in one embodiment, a multi-detector inverse fan beam (MIFB) 50 is projected along x-axis 52 onto the X-Y plane. In one embodiment, MFXS 12 emits radiation sequentially from a plurality of focus points 54. More specifically, MFXS 12 includes an anode 56 and a plurality of focus points 54 arranged along a length of anode 56 colinear with a y-axis 58 of MFXS 12. Each focus point 54 is sequentially activated to emit an x-ray fan beam. For example, focus point $F_1$ emits fan beam MIFB 50 that extends between and is detected by coherent x-ray scatter detector $D_1$ through and including coherent x-ray scatter detector $D_{13}$ and includes a plurality of pencil primary beams 60. Focus points 54 are denoted $F_1, F_2, \ldots F_i, \ldots F_n$ with a running index i. Primary collimator 18 is configured to select from the radiation emitted at each focus point 54, primary beams that are directed to a series of convergence points 62 labeled $O_1, O_2, \ldots, O_j, \ldots O_m$ with a running index j regardless of which focus point 54 is activated. Ten primary beams 60 are shown in FIG. 2 with each primary beam 60 emitted from focus point $F_1$ directed to a corresponding convergence point $O_1, O_2, \ldots, O_j, \ldots O_{10}$ positioned along a line parallel to the y-axis at a coordinate X=L with focus point $F_1$ activated.

A plurality of discrete coherent x-ray scatter detectors 24 labeled discrete coherent x-ray scatter detectors $D_1, D_2, \ldots D_j, \ldots D_k$ with a running index j are positioned at a suitable or desirable distance in a direction along the Z-axis from a corresponding convergence point 62 to record coherent scatter at an angle θ from primary beam $P_{ij}$ in discrete coherent x-ray scatter detector $D_j$. In one embodiment, this distance is about 30 mm for a scatter angle of about 0.037 radians at a distance of about 750 mm between a scatter center and a corresponding coherent x-ray scatter detector $D_j$. A combination of the MFXS and the discrete coherent x-ray scatter detectors facilitates examining a volume of an object positioned within examination area without any dead area from which no XDI signal is detected or measured.

As primary beam 60 labeled $P_{ij}$ propagates through an object (not shown) positioned within examination area 14, primary beam $P_{ij}$ interacts with the object to produce coherent scatter that may be detected in coherent x-ray scatter detectors $D_{j+1}, D_{j+2}, D_{j-1}$, and/or $D_{j-2}$, for example. Primary beams $P_{11}, P_{12}, P_{13}, P_{14}, P_{15}, \ldots P_{1m}$ are emitted from focus point $F_1$ and directed to corresponding convergence points $O_1, O_2, O_3, O_4, O_5, \ldots O_m$, respectively. As each primary beam $P_{11}, P_{12}, P_{13}, P_{14}, P_{15}, \ldots P_{1m}$ moves through examination area 14, each primary beam $P_{11}, P_{12}, P_{13}, P_{14}, P_{15}, \ldots P_{1m}$ collides with and/or interacts with an object (not shown) positioned within examination area 14 to produce coherent scatter (not shown) that is detectable at one or more coherent x-ray scatter detectors $D_1, D_2, D_3, D_4, D_5, \ldots D_k$, for example.

In one embodiment, MFXS 12 is positioned on the y-axis (x=0) of a Cartesian coordinate system. Each focus point 54 has a position on a grid having a pitch, $P_s$. Further, convergence points 62 lie parallel to the y-axis at coordinate X=L, and each convergence point 62 has a position on a grid having a pitch, $P_t$. In a particular embodiment, for an XDI checked baggage screening system, L has a value in a range between about 2000 millimeters (mm) and about 2500 mm, $P_s$ is about 25 mm, and $P_t$ is about 50 mm to about 200 mm. A plurality of coherent x-ray scatter detectors 24 are positioned at the same y-coordinate as convergence points 62. One pair of coherent x-ray scatter detectors 24 may be associated with a corresponding convergence point 62 with the pair of coherent x-ray scatter detectors 24 positioned on both sides of the X-Y plane. In a further embodiment, thirteen (13) convergence points are used to allow for several convergence point position arrangements to incorporate a different number of coherent x-ray scatter detectors 24. If all convergence points 62 have detector pairs then security detection system 10 may include twenty-six (26) coherent x-ray scatter detectors 24. In alternative embodiments, fewer coherent x-ray scatter detectors 24 may be positioned at convergence point positions 1, 3, 5, 7, 9, 11, and 13, at convergence point positions 1, 4, 7, 10, and 13, or at convergence point positions 1, 5, 9, and 13 to account for manufacturing and/or cost constraints. An MIFB configuration including 13 convergence points spanning a width in the Y direction in total of 2000 mm requires a fan angle from each focus point 54 of about 55° in the y-axis direction.

A right-most detector $D_{13}$ detects a plurality of primary beams 60 labeled $P_{113}, P_{213}, \ldots P_{ij}, \ldots P_{913}$, alternatively referred to herein as an inverse fan beam bundle 70 of primary beams, from each focus point 54 denoted $F_1, F_2, \ldots F_i, \ldots F_9$ of MFXS 12 that are transmitted by primary collimator 18. Inverse fan beam bundle 70 is significantly narrower than a width of examination area 14. MFXS 12, as depicted in FIG. 2 is not shown to scale for clarity's sake, and may be smaller than shown. Moreover, only 13 convergence points 62 are shown although, as described above, in practice the number of convergence points 62 can be much greater. Further, the scatter signal is proportional to a number of coherent x-ray scatter detectors 24 incorporated into security detection system 10.

Several inverse fan beam bundles 70 of primary beams directed towards a corresponding convergence point $O_j$ are detected by a corresponding coherent x-ray scatter detector $D_j$. During a scan of the object positioned within examination area 14, during which each focus point 54 of MFXS 12 is sequentially activated, the object section is completely irradiated and scatter signals are measured from an entire width of the object. In this embodiment, no mechanical movements are required to achieve a complete 2-D scan of the object. MFXS 12 achieves this with only a small x-ray source dimension along the y-axis. In the exemplary embodiment, MFXS has a length along the y-axis of less than about 500 mm. A small x-ray source dimension is advantageous from the viewpoints of cost and reliability.

In one embodiment, each point in an object section is seen by at least M coherent x-ray scatter detectors. It can be shown that this redundancy condition is fulfilled when the regular spacing, P, between adjacent coherent x-ray scatter detectors satisfies the equation:

$$P = \frac{W_s \cdot V}{M \cdot U},\qquad \text{Eq. 1}$$

where $W_s$ is a lateral extent of the plurality of focus points, U is a distance from y-axis 58 of MFXS 12 to a top surface 72 of examination area 14, and V is a distance from top surface 72 to a coherent x-ray scatter detector plane at X=L.

In one embodiment suitable for carry-on baggage screening, $W_s$ is approximately 400 mm, U is approximately 1400 mm and V is approximately 700 mm. Hence, a coherent x-ray scatter detector pitch or spacing, P, from Equation 1 is 200 mm for M=1 and 100 mm for M=2. With M=1, all points of the object section are scanned by at least one of the plurality of primary beams emitted by the plurality of focus points onto one coherent x-ray scatter detector $D_j$. With M=2, all points of the object section are scanned by at least two of the plurality of primary beams emitted by the plurality of focus points onto one coherent x-ray scatter detector $D_j$.

A total lateral extent of the detector array, i.e., a distance from coherent x-ray scatter detector $D_1$ to coherent x-ray scatter detector $D_{13}$, is approximately 2200 mm, and corresponds to 23 coherent x-ray scatter detectors 24 having a detector pitch or spacing of 100 mm. The spacing between adjacent coherent x-ray scatter detectors 24 is sufficiently large such that cross-talk scatter from a certain primary beam $P_{ij}$, measured by a coherent x-ray scatter detector $D_{j+1}$ adjacent to coherent x-ray scatter detector $D_j$ to which primary beam $P_{ij}$ is directed, has such a large scatter angle that its coherent scatter contribution can be neglected.

Figure 3:
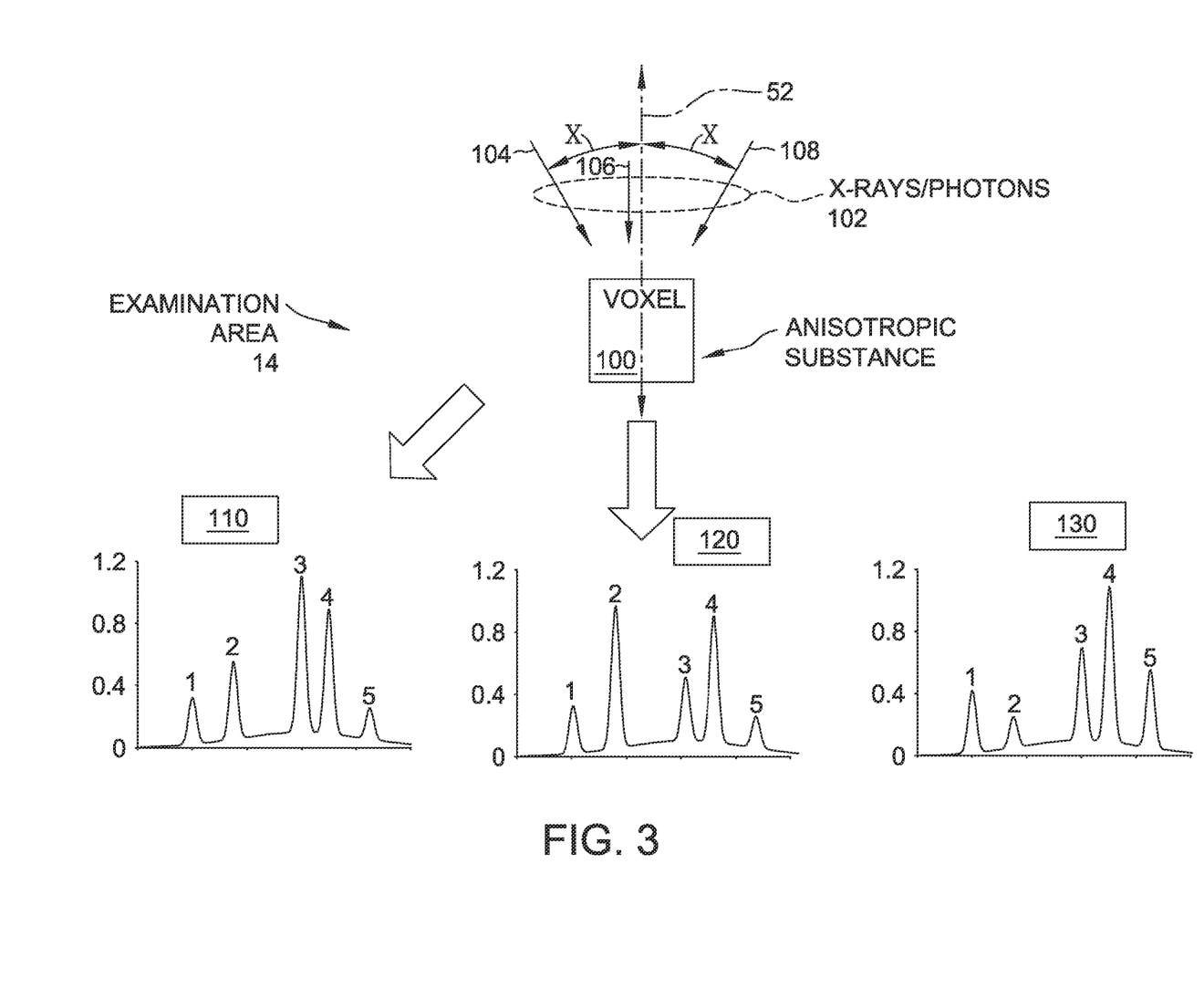
FIG. 3 is a schematic view of an exemplary voxel irradiated with photons from a plurality of directions and the associated XDI profiles.

FIG. 3 is a schematic view of an exemplary voxel 100 irradiated with photons 102 from a plurality of directions and the associated XDI profiles 110, 120, and 130. Voxel 100 is a volumetric portion of an object that includes at least one substance (neither shown). Photons 102 irradiate voxel 100 through primary beam 60 (shown in FIG. 2). Specifically, photons 104, photons 106, and photons 108 irradiate voxel 100 from different, predetermined directions, each direction defined by an angle of incidence χ with respect to system axis 52. Therefore, in MIFB XDI security detection system 10, data are acquired over a range of angles of incidence χ between primary beam 60 and system axis 52, rather than using merely a single angle.

Scattering of photons 104, 106, and 108 into one of discrete coherent x-ray scatter detectors 24 (shown in FIGS. 1 and 2). Processor 44 (shown in FIG. 1) generates angle-dependent XDI profiles 110, 120, and 130. XDI profiles 110, 120, and 130 are associated with photons 104, 106, and 108, respectively. Each of XDI profiles 110, 120, and 130 includes five Bragg peaks that show photon intensity (ordinate) as a function of scattering angle (abscissa). XDI profiles 110, 120, and 130 are dissimilar and while each of peaks 1, 2, 3, 4, and 5 may vary in intensity, i.e., height, the peaks are at substantially similar scattering angle values.

In the exemplary embodiment, MIFB XDI security detection system 10 is a five-dimensional system. The five dimensions are defined as the three orthogonal spatial dimensions (x, y, and z), a momentum dimension (q), and an angle of incidence χ dimension through the separate measurement and storage of angle-dependent XDI profiles 110, 120, and 130 of the same object voxel 100 that are acquired over a range of different irradiation directions χ. XDI profiles 110, 120, and 130 belonging to the same irradiation direction χ are stored separately (x, y, z, q, χ) as a function of angle of incidence χ to preserve information about the direction of primary beam 60 in which photons 104, 106, and 108 originated relative to system axis 52.

In general, for liquid, amorphous and micro-crystalline powder samples there is no preferred orientation direction and the associated XDI profile is independent of irradiation angle. However, voxels containing an appreciable amount of single-crystal material have a statistically-varying preferred orientation direction and the XDI profile changes according to the relative angles of the primary x-ray beam to this orientation direction and according to the number of crystallites included in a voxel signal. Therefore, one possible cause of the dissimilarity of XDI profiles 110, 120, and 130 may be that there is an anisotropic arrangement of crystallites in voxel 100. One example of substances whose XDI profiles vary with angle is the class of anisotropic substances, including coarse grain powders. They have a relatively high degree of single crystal material compared to isotropic substances such as fine powders. In the exemplary embodiment, a coarse grain material occupies voxel 100. Angle-dependent XDI screening through MIFB XDI security detection system 10 enhances detection performance of materials for which the XRD profiles measured from different irradiation directions vary. Therefore, MIFB XDI security detection system 10 facilitates an XDI method whereby the angle dependence of XDI profiles 104, 106, and 108 is explicitly considered in the threat/no threat classification procedure.

In the exemplary embodiment, the classification procedure used by MIFB XDI security detection system 10 incorporates a "similarity" feature, derived by comparing angle-dependent XDI profiles 104, 106, and 108 with one another.

One example of a classification procedure taking explicit account of angle information includes considering a "similarity" feature that can be extracted by comparing the three XDI profiles 104, 106, and 108 with one another. A possible "similarity" measure is provided by the cross-correlation coefficient, Fab(q), which is described in standard statistical works. The functions a(q) and b(q) are those whose similarity is to be determined; and q is the momentum variable. There are in all three possibilities, i.e., $F_{104\text{-}106}(q)$, $F_{104\text{-}108}(q)$ and $F_{106\text{-}108}(q)$. In this example, the numerical values of the cross-correlation coefficients are: $F_{104\text{-}106}(q)$=0.85, $F_{104\text{-}108}(q)$=0.89, and $F_{106\text{-}108}(q)$=0.79. The overall "similarity" is 0.84 through taking the average of the three values.

A "similarity" value of unity (1) indicates that XDI profiles 104, 106, and 108 are independent of irradiation direction and a lower "similarity" value indicates that the profiles measured at different angles differ from one another. When the "similarity" value is low, the classification procedure indicates that the relative heights of the Bragg peaks are no longer a reliable guide to the nature of the material. In this case, knowledge of the "similarity" value may facilitate avoiding false classification originating in a spurious peak height determination. Moreover, from this information, the class of materials that are known to deliver a high "similarity" feature can be entirely excluded from further evaluation, e.g., amorphous materials such as liquids, emulsions, and small grain crystal-line materials. The "similarity" feature provides additional information which, in conjunction with other features, is valuable for improving the detection performance of the classification procedure for some materials. The library of XDI measurements for known substances has to be extended to include "similarity" information along with the other features.

Figure 4:
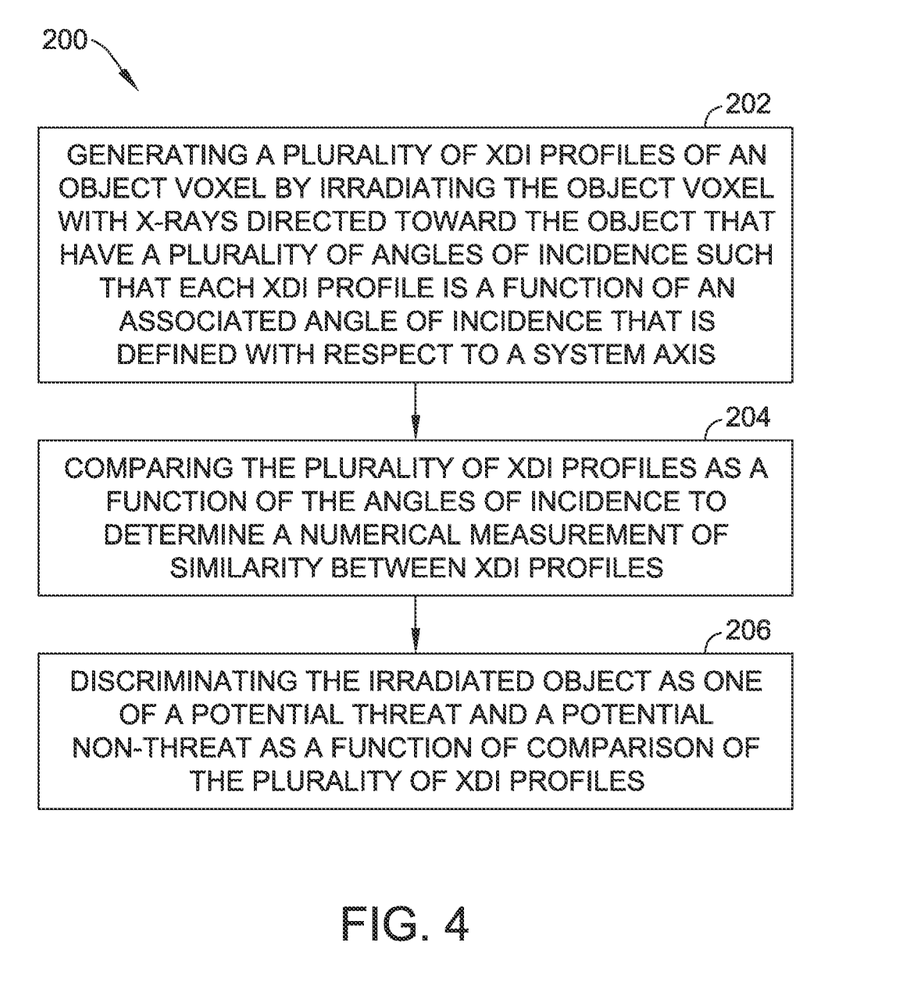
FIG. 4 is a flow chart of an exemplary method of operating the security detection system shown in FIGS. 1 and 2.

FIG. 4 is a flow chart of an exemplary method 200 of operating security detection system 10 (shown in FIGS. 1 and 2), i.e., a method 200 of performing a security screen of an object (not shown) that includes at least one substance (not shown). In method 200, a plurality of XDI profiles 110, 120, and 130 (all shown in FIG. 3) of an object voxel 100 (shown in FIG. 3) are generated 202. Object voxel 100 is irradiated with x-rays 104, 106, and 108 (all shown in FIG. 3) directed toward the object. X-rays 104, 106, and 108 have a plurality of angles of incidence $\chi$. Each XDI profile 110, 120, and 130 is a function of an associated angle of incidence $\chi$ and each angle of incidence $\chi$ is defined with respect to system axis 52 (shown in FIG. 3). XDI profiles 110, 120, and 130 are compared 204 to each other as a function of the angles of incidence $\chi$ to determine a numerical measurement of similarity between XDI profiles 110, 120, and 130. A discrimination is made 206 between at least one isotropic substance having a high similarity value and at least one anisotropic substance having a low similarity value to determine if the irradiated object is one of a potential threat and a potential non-threat as a function of the comparison of the plurality of XDI profiles 110, 120, and 130.

The above described angle dependent multi-detector inverse fan beam (MIFB) x-ray diffraction imaging (XDI) system described herein facilitates cost-effective enhanced integration of angle data, thus enhancing overall performance of a security scanning system. Specifically, in contrast to many known security scanning systems, the MIFB XDI security screening system as described herein facilitates exploiting angle-dependent XDI data acquired over a range of angles between the primary beam and the system axis, rather than merely using a single angle. More specifically, the MIFB XDI security screening system as described herein using angle-dependent XDI screening enhances detection performance of materials for which the XRD profiles measured from different irradiation directions vary. As such, the MIFB XDI security screening system as described herein facilitates classification into threat/no threat substances explicitly taking into account the angular dependence of XDI data in the form of XDI profiles acquired from different irradiation directions for the same voxel. Therefore, detection of substances, such as the class of anisotropic substances including coarse-grain powders that have XDI profiles that vary with angle because they have a relatively high degree of single crystal material as compared to isotropic substances, such as fine powders.

A technical effect of the systems and methods described herein includes at least one of: (a) exploiting angle-dependent XDI data acquired over a range of angles between the primary beam and the system axis, rather than merely using a single angle; (b) enhancing detection performance of materials for which the XRD profiles measured from different irradiation directions vary; (c) facilitating classification into threat/no threat substances explicitly taking into account the angular dependence of XDI data in the form of XDI profiles acquired from different irradiation directions for the same voxel; and, (d) facilitating detection of anisotropic substances including coarse-grain powders that have XDI profiles that vary with angle.

Exemplary embodiments of angle dependent multi-detector inverse fan beam (MIFB) x-ray diffraction imaging (XDI) systems are described above in detail. The methods and systems are not limited to the specific embodiments described herein, but rather, components of systems and/or steps of the methods may be utilized independently and separately from other components and/or steps described herein. For example, the methods may also be used in combination with other detection systems and methods, and are not limited to practice with only the detection systems and methods as described herein. Rather, the exemplary embodiment may be implemented and utilized in connection with many other XDI security screening system applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An x-ray diffraction imaging (XDI) system having a system axis, said system comprising:
   at least one x-ray source configured to generate x-rays directed toward an object that includes at least one substance, wherein said at least one x-ray source is further configured to irradiate at least one voxel defined within the object with x-rays arriving from a plurality of directions, each direction defined by an angle of incidence with respect to the system axis;
   at least one detector configured to detect scattered x-rays after the x-rays have passed through the object; and
   at least one processor coupled to said at least one detector, said at least one processor programmed to generate a plurality of XDI profiles of the object voxel, wherein each XDI profile is a function of an associated angle of incidence.

2. The XDI system in accordance with claim 1, wherein said XDI system is a five-dimensional system, the five dimensions defined as three orthogonal spatial dimensions, a momentum dimension, and an angle of incidence dimension.

3. The XDI system in accordance with claim 1 further comprising at least one memory device coupled to said at least one processor, wherein:
   said at least one processor is configured to sort the plurality of XDI profiles as a function of the angle of incidence; and
   said at least one memory device is configured to store the plurality of XDI profiles as a function of the angle of incidence.

4. The XDI system in accordance with claim 3, wherein said at least one processor is further configured to use the plurality of XDI profiles sorted as a function of the angles of incidence to facilitate discrimination of the irradiated object as one of a potential threat and a potential non-threat.

5. The XDI system in accordance with claim 3, wherein said at least one processor is further configured to compare the plurality of XDI profiles of the at least one voxel as a function of the angles of incidence to determine a numerical measurement of similarity between the plurality of XDI profiles.

6. The XDI system in accordance with claim 5, wherein said at least one processor is further configured to discriminate between at least one irradiated substance with a high similarity value from at least one irradiated substance with a low similarity value.

7. The XDI system in accordance with claim 5, wherein said at least one processor is further configured to discriminate between anisotropic substances and isotropic substances.

8. The XDI system in accordance with claim 1 further comprising an examination area configured to receive the object, wherein:
   said at least one x-ray source comprises a multi-focus x-ray source (MFXS); and
   said at least one detector comprises a plurality of coherent x-ray scatter detectors positioned with respect to the examination area, said plurality of coherent x-ray scatter detectors configured to detect coherent scatter rays from a plurality of primary beams as the plurality of primary beams propagate through the object positioned within the examination area.

9. The XDI system in accordance with claim 8, wherein said MFXS comprises an anode and a plurality of focus points arranged along a length of said anode colinear with an axis of said MFXS orthogonal to the system axis, each focus point of the plurality of focus points configured to be sequentially activated to emit an x-ray fan beam including a plurality of primary beams.

10. The XDI system in accordance with claim 1, wherein said XDI system is a multiple inverse fan beam (MIFB) XDI system.

11. One or more non-transitory computer-readable storage media having computer-executable instructions embodied thereon, wherein when executed by at least one processor, the computer-executable instructions cause the processor to:
   generate a plurality of XDI profiles of an object voxel, wherein the object voxel is irradiated with x-rays directed toward an object that includes at least one substance, the x-rays having a plurality of angles of incidence, each XDI profile a function of an associated angle of incidence, each angle of incidence defined with respect to a system axis;
   compare the plurality of XDI profiles; and
   discriminate the irradiated object as one of a potential threat and a potential non-threat as a function of comparison of the plurality of XDI profiles.

12. One or more non-transitory computer-readable storage media having computer-executable instructions embodied thereon in accordance with claim 11, wherein when executed by at least one processor, the computer-executable instructions cause the processor to store XDI profile data within a five-dimensional system, the five dimensions defined as three orthogonal spatial dimensions, a momentum dimension, and an angle of incidence dimension.

13. One or more non-transitory computer-readable storage media having computer-executable instructions embodied thereon in accordance with claim 11, wherein when executed by at least one processor, the computer-executable instructions cause the processor to compare the plurality of XDI profiles of the at least one voxel as a function of the angles of incidence to determine a numerical measurement of similarity between the plurality of XDI profiles.

14. One or more non-transitory computer-readable storage media having computer-executable instructions embodied thereon in accordance with claim 13, wherein when executed by at least one processor, the computer-executable instructions cause the processor to discriminate between at least one irradiated substance with a high similarity value from at least one irradiated substance with a low similarity value.

15. One or more non-transitory computer-readable storage media having computer-executable instructions embodied thereon in accordance with claim 14, wherein when executed by at least one processor, the computer-executable instructions cause the processor to discriminate between at least one isotropic substance having a high similarity value and at least one anisotropic substance having a low similarity value.

16. A method of performing a security screen of an object that includes at least one substance, said method comprising:
   generating a plurality of XDI profiles of an object voxel, wherein the object voxel is irradiated with x-rays directed toward the object, the x-rays having a plurality of angles of incidence, each XDI profile a function of an associated angle of incidence, each angle of incidence defined with respect to a system axis;
   comparing the plurality of XDI profiles; and
   discriminating the irradiated object as one of a potential threat and a potential non-threat as a function of comparison of the plurality of XDI profiles.

17. The method in accordance with claim 16 further comprising storing the XDI profile data within a five-dimensional system, the five dimensions defined as three orthogonal spatial dimensions, a momentum dimension, and an angle of incidence dimension.

18. The method in accordance with claim 16 further comprising comparing the plurality of XDI profiles of the at least one voxel as a function of the angles of incidence to determine a numerical measurement of similarity between the plurality of XDI profiles.

19. The method in accordance with claim 16 further comprising discriminating between at least one irradiated substance with a high similarity value from at least one irradiated substance with a low similarity value.

20. The method in accordance with claim 19 further comprising discriminating between at least one isotropic substance having a high similarity value and at least one anisotropic substance having a low similarity value.

* * * * *